United States Patent [19]
Feit

[11] 4,285,905
[45] Aug. 25, 1981

[54] METHOD AND ARTICLE FOR DISPERSING A VOLATILIZABLE COMPOUND IN AN ENVIRONMENT

[76] Inventor: Richard Feit, Avant, Inc., 633 Skokie Blvd., Northbrook, Ill. 60062

[21] Appl. No.: 195,823

[22] Filed: Oct. 10, 1980

[51] Int. Cl.$^3$ .................... A61L 9/01; A61L 9/02; A61L 9/04
[52] U.S. Cl. .................... 422/4; 239/60; 252/522 A; 264/299; 264/338; 422/5; 422/123; 422/124; 422/125; 422/306; 424/18; 424/23; 424/76
[58] Field of Search .............. 422/4, 5, 123, 124, 422/125, 305, 306; 252/522 A; 424/18, 23, 76; 264/299, 338; 239/60

[56] References Cited
U.S. PATENT DOCUMENTS

| | | | |
|---|---|---|---|
| Re. 18,915 | 8/1933 | Ell | 167/3 |
| 321,368 | 6/1885 | Jassa | 424/76 |
| 659,621 | 10/1900 | Kelsey | 424/76 |
| 1,083,561 | 1/1914 | Rising | 424/18 |
| 1,408,535 | 3/1922 | Ressler | 424/76 |
| 1,641,183 | 9/1927 | Martin et al. | 422/4 X |
| 1,847,233 | 3/1932 | Bilde . | |
| 2,220,583 | 11/1940 | Schnebly et al. | 219/45 |
| 2,238,476 | 4/1941 | Monteith | 299/24 |
| 2,251,058 | 7/1941 | Kirkman | 422/5 X |
| 2,500,896 | 4/1950 | Drake | 299/20 |
| 2,585,289 | 2/1952 | Wallace | 422/305 X |
| 2,742,342 | 4/1956 | Dew et al. | 21/53 |
| 3,049,399 | 8/1962 | Gamson et al. | 21/53 |
| 3,371,984 | 3/1968 | Kelly et al. | 21/53 |
| 3,418,068 | 12/1968 | Gilbertson | 21/74 |
| 3,954,963 | 5/1976 | Kuderna | 252/522 A X |
| 4,067,692 | 1/1978 | Farris | 21/74 R |
| 4,146,566 | 3/1979 | Gaiser | 422/123 X |
| 4,166,087 | 8/1979 | Cline et al. | 422/306 X |

FOREIGN PATENT DOCUMENTS
3885 of 1876 United Kingdom .
570239 6/1945 United Kingdom .

*Primary Examiner*—Barry Richman
*Attorney, Agent, or Firm*—Neuman, Williams, Anderson & Olson

[57] ABSTRACT

A solid unitary article and method for dispersing a volatilizable compound in an environment. A solid article consisting essentially of from about 25 to 30 wt. % initially particulate calcium sulfate having a loose bulk density of from about 0.85 to 0.95 gm/cm$^3$;

about 25 to 30 wt. % initially particulate calcium sulfate having a loose bulk density of from about 0.70 to 0.75 gm/cm$^3$;

about 2 to 4 wt. % initially particulate hydrous calcium sulfate having a loose bulk density of from about 0.75 to 0.85 gm/cm$^3$;

about 0.5 to 1 wt. % emulsifier;

about 6 to 7 wt. % volatilizable compound; and about 30 to 35 wt. % water is exposed to said environment to effect dispersal of the volatilizable compound. A process for preparing said solid article and a kit for effecting dispersal of volatilizable compound into an environment are also provided.

The solid article and method are particularly efficacious in dispersing a heat-stable, volatile fragrance compound in an environment.

38 Claims, 2 Drawing Figures

METHOD AND ARTICLE FOR DISPERSING A VOLATILIZABLE COMPOUND IN AN ENVIRONMENT

BACKGROUND OF THE INVENTION

1. Field of the Invention

This invention relates generally to dispersing a volatilizable compound in an environment, and particularly relates to dispersing a heat-stable, volatile fragrance.

2. Background of the Invention

Dispersal of volatilizable compounds, through evaporation and/or vaporization, into an environment from a substrate or carrier has long been practiced for a variety of purposes. As early as 1876, British Pat. No. 3885 disclosed an improvement in the treating of tobacco comprising providing a permeable receptacle which enclosed and contained an efflorescent salt or a porous body, which salt or body was charged by the user with a compound which exudes either a liquid or vapor through the receptacle, which was placed in the smoker's pouch or tobacco jar. British Pat. No. 570,239 disclosed an efflorescent block for the controlled evolution and dissemination of ammonia into a surrounding body of gas, such as the atmosphere in a relatively confined space, which gradually crumbled and disintegrated so as to cause fresh areas of the block composition continuously to become exposed to the air, whereby a steady evolution of the ammonia was secured. Kelly, U.S. Pat. No. 3,371,984, disclosed a solid air odorizing composition in tablet form, for use in combination with a vacuum cleaner, which was "adapted to controllably release a pleasing odor." Claim 1. The tablet comprised a hydrated salt which irreversibly lost its water of hydration with which a fragrance was mixed, which composition was then compacted to the tablet form. Col. 2, line 66 -col. 3, line 5. The loss of water resulted in the slow crumbling or disintegration of the tablet, providing a fresh surface necessary for fragrance release of about four weeks duration in vacuum cleaner use. Example 2.

While these means for effecting dispersal of volatilizable compounds into an environment, e.g., a surrounding body of gas, such as the atmosphere in a relatively confined space, are thus kwown, they exhibit serious drawbacks. British Pat. No. 3885 requires the use of a two element combination of container and absorbant substrate, which must be charged with the volatilizable material by the user at the inception of use and, apparently, frequently thereafter. British No. 570,239 and Kelly U.S. Pat. No. 3,371,984 are unable to provide persistent, long-term dispersal of a volatilizable compound, particularly in an environment wherein the dispersing article is exposed to a gaseous flow, such as convective flow from a heat source or forced flow, such as from a forced-air furnace. Further, their mechanism resulting in the efflorescence, crumbling or disintegration of the substrate or carrier block creates a litter problem which is particularly troublesome in home or office. Finally, Kelly can provide no long-term, persistent release of volatilizable compound.

The optimum combination of properties for a method and article for dispersing volatilizable compounds in an environment would comprise:

(1) An article incorporating the volatilizable compound which requires no charging of said compound by the user at the inception of use or thereafter;

(2) The article would be a solid, coherent article, rather than a granular or particulate substance, which could be utilized without need for an enclosing receptacle or container, such as is required for such a granular or particulate substance;

(3) The article would remain solid and coherent throughout its useful life, and would not disintegrate, crumble, decompose or effloresce;

(4) The article would provide persistent, long-term dispersal of the volatilizable compound in an environment; and (5) The article would further provide dispersal of the volatilizable compound in response to a gaseous flow in said environment, including convective and forced flow.

None of the methods and articles for dispersing a volatilizable compound known to the art, however, provide this optimum combination of properties with respect to effecting such dispersal in an environment.

SUMMARY OF THE INVENTION

The present invention relates to a method and article for dispersing a volatilizable compound in an environment. The method of the invention consists essentially of exposing a solid article comprising the volatilizable compound to said environment to effect dispersal of said compound.

The solid articles of the present invention consist essentially of the following components:

from about 25 to 30 wt. % initially particulate calcium sulfate having a loose bulk density of from about 0.85 to 0.95 gm/cm$^3$;

about 25 to 30 wt. % initially particulate calcium sulfate having a loose bulk density of from about 0.70 to 0.75 gm/cm$^3$;

about 2 to 4 wt % initially particulate hydrous calcium sulfate having a loose bulk density of from about 0.75 to 0.85 gm/cm$^3$;

about 0.5 to 1 wt. % emulsifier;

about 6 to 7 wt. % volatilizable compound; and about 30 to 35 wt. % water.

A process for preparing the solid articles for dispersing a volatilizable compound of the invention comprises the steps of:

(a) Combining from about 0.5 to 1 wt. % emulsifier and from about 6 to 7 wt. % of a volatilizable compound;

(b) Agitating and mixing said combined emulsifier and volatilizable compound until a uniform emulsion is formed;

(c) Combining with agitation the emulsion of step (b) with from about 30 to 35 wt. % water;

(d) Adding with agitation from about 2 to 4 wt. % particulate hydrous calcium sulfate having a loose bulk density of from about 0.75 to 0.85 gm/cm$^3$ to the mixture of step (c);

(e) Adding with agitation to the mixture of step (d) from about 25 to 30 wt. % particulate calcium sulfate having a loose bulk density of from about 0.85 to 0.95 gm/cm$^3$, and from about 25 to 30 wt. % particulate calcium sulfate having a loose bulk density of from about 0.70 to 0.75 gm/cm$^3$;

(f) Agitating the mixture of step (e) until a smooth slurry is formed;

(g) Placing said slurry in a molding zone; and (h) Allowing said slurry to set in said molding zone until a solid article is formed.

A kit of the invention for effecting dispersal of a volatilizable compound into an environment, which demonstrates excellent shelf life without diminution of the long-term persistence of the compound dispersal, which comprises:

(1) a solid volatilizable compound consisting essentially of
- from about 25 to 30 wt. % initially particulate calcium sulfate having a loose bulk density of from about 0.85 to 0.95 gm/cm$^3$;
- about 25 to 30 wt. % initially particulate calcium sulfate having a loose bulk density of from about 0.70 to 0.75 gm/cm$^3$;
- about 2 to 4 wt. % initially particulate hydrous calcium sulfate having a loose bulk density of from about 0.75 to 0.85 gm/cm$^3$;
- about 0.5 to 1 wt. % emulsifier;
- about 6 to 7 wt. % volatilizable compound; and
- about 30 to 35 wt. % water; and (2) package means slightly larger than said article, said means encasing said article, said means being sealed and being made of a flexible, tearable barrier film, which seals upon the application of heat and pressure, so that the envelope may be opened by being torn and being substantially unaffected by and substantially impermeable to said volatilizable compound and the vapors thereof, and being of a strength to resist the vapor pressure thereof.

The present invention overcomes the drawbacks of the prior art by providing a method and article for dispersing volatilizable compounds in an environment which requires no charging of said compound to the article by the user at the inception of use or thereafter, which is a solid, coherent article which may be utilized without providing an enclosing receptacle or container therefore, which remains solid and coherent throughout its useful life, and does not disintegrate, crumble, decompose or effloresce, which provides persistent, long-term dispersal of the volatilizable compound in an environment, and which further provides dispersal of the volatilizable compound in response to a gaseous flow in an environment, including convective and forced flow.

Accordingly, it is an object of this invention to provide an improved method of dispersing a volatilizable compound in an environment which provides long-term, persistent release of that compound. It is a further object of this invention to provide a solid article for dispersing a volatilizable compound in an environment which requires no charging of said compound by the user at the inception of use or thereafter, and which may be utilized without need for a receptacle or container therefore.

It is another object of this invention to provide a solid article for dispersing a volatilizable compound in an environment which does not disintegrate, crumble, decompose or effloresce, yet provides persistent, long-term dispersal of the volatilizable compound in an environment.

It is yet another object of this invention to provide a novel process for preparing a solid article for dispersing a volatilizable compound in an environment.

It is a further object of this invention to provide a novel kit for dispersing a volatilizable compound in an environment which demonstrates excellent shelf life without effecting substantial diminution of the long-term persistence of the compound dispersal.

Other objects and advantages of this invention will become apparent upon reading the following detailed description and appended claims.

DESCRIPTION OF THE PREFERRED EMBODIMENT

The preferred article of the invention for dispersing a volatilizable compound consists essentially of
- from about 25 to 30 wt. % initially particulate calcium sulfate having a loose bulk density of from about 0.85 to 0.95 gm/cm$^3$;
- about 25 to 30 wt. % initially particulate calcium sulfate having a loose bulk density of from about 0.70 to 0.75 gm/cm$^3$;
- about 2 to 4 wt. % initially particulate hydrous calcium sulfate having a loose bulk density of from about 0.75 to 0.85 gm/cm$^3$;
- about 0.5 to 1 wt. % emulsifier;
- about 6 to 7 wt. % volatilizable compound; and
- about 30 to 35 wt. % water.

The preferred method for dispersing a volatilizable substance into an environment comprises exposing the preferred article to said environment.

While not wishing to be bound by this explanation, it appears that the unique properties of the solid article of the invention result from the formation of a microcellular structure in the article during preparation, which in turn is believed to result from the agitation-caused aeration of the component slurry from which the article is cast, and from the resultant setting or hardening of the slurry in the molding zone. These microcells, and to a lesser degree, inter-connecting submicroscopic veins also formed during preparation of the article, trap, partially encapsulate and retain the emulsifier volatilizable compound. On exposure to the environment, evaporation and/or vaporization of the compound commences at the outer surfaces of the article. As the compound slowly volatilizes and disperses from said surfaces, a wicking action, fed through the microcellular structure, commences. This slowly carries additional volatilizable compound to the article-environment interface, where evaporation and/or vaporization continues the cycle.

The rapidity of the wicking action appears to be directly related to the rate of volatilization from the surface, which in turn is directly related to air flow, air temperature and relative humidity of the air. Thus, speed of compound volatilization can be affected by varying the air flow to which the solid article is exposed in the environment, separately or concomitantly with variation of air temperature and humidity.

The preferred embodiments of the invention comprise the exposure of a solid article of the preferred compositions to a gaseous flow in the environment. The gaseous flow may result from any source, singly or in combination with another source. Convective flow, such as results from heat generated by an incandescent or other light fixture, or from any other heat source, such as an electric heater, comprises such gaseous flow. Forced flow, such as that caused by a forced-air heating or cooling system, fan, blower or other motive source, also comprises gaseous flow contemplated by the invention. A combination of convective and forced flow in the environment would also serve to control the dispersal of the volatilizable compound. The solid article may be placed in direct proximity to the flow source, or may be placed at any other location in the flow path.

Of course, it is to be understood that evporation and/or vaporization of the volatilizable compound will take place without any gaseous flow in the environment-dispersion will occur in quiescent air, albeit at a lower rate.

The components making up the solid article composition are known chemicals which may be procured from standard chemical sources. The calcium sulfate components comprise ground plasters in a particulate form, having the loose bulk densities disclosed. It is preferable to use ground plasters having a particle size such that greater than 97% thereof will fit through a 100-mesh screen. The hydrous calcium sulfate component similarly comprises a ground gypsum in particulate form, with the loose bulk density disclosed. As with the ground plaster components, the gypsum should be a particulate of size such that greater than 97% thereof will fit through a 100-mesh screen.

Any of the well-known emulsifiers or surface active agents capable of forming an emulsion of the volatilizable compound and water may be utilized in the invention, provided further that it is compatible with the calcium sulfate and hydrous calcium sulfate components. Non-ionic emulsifying agents such as the polyoxyethylene condensates are particularly efficacious.

Polyoxyethylene condensates may be represented by the general formula:

where R is the residue of a fatty alcohol containing 10–18 carbon atoms, an alkyl phenol, a fatty acid containing 10–18 carbon atoms, an amide, an amine, or a mercaptan, and where n is an integer of 1 or above. Some specific examples of polyoxyethylene condensates which can be used include polyoxyethylene aliphatic ethers such as polyoxyethylene lauryl ether, polyoxyethylene oleyl ether, polyoxyethylene hydroabietyl ether and the like; polyoxyethylene alkaryl ethers such as polyoxyethylene nonylphenyl ether, polyoxyethylene octylphenyl ether and the like; polyoxyethylene esters of higher fatty acids such as polyoxyethylene laurate, polyoxyethylene oleate and the like as well as condensates of ethylene oxide with resin acids and tall oil acids; polyoxyethylene amide and amine condensates such as N-polyoxyethylene lauramide, and N-lauryl-N-polyoxyethylene amine and the like; and polyoxyethylene thioethers such as polyoxyethylene n-dodecyl thioether.

The non-ionic emulsifying agents which can be used also include a series of surface active agents known as "Pluronics." The "Pluronics" have the general formula:

where a, b, and c are integers of 1 or above. As b increases, the compounds become less water soluble or more oil soluble and thus more hydrophobic when a and c remain substantially constant.

In addition, a series of ethylene oxide adducts of acetylenic glycols sold commercially under the name "Surfynols," are highly suitable. This class of compounds can be represented by the formula in which $R_1$ and $R_4$ are alkyl radicals containing from three to 10 carbon atoms, $R_2$ and $R_3$ are selected from the group consisting of methyl and ethyl, x and y have a sum in the range of three to 60, inclusive.

The volatilizable compound includes any compound which will volatilize under atmospheric pressure conditions, including those which will volatilize at ambient temperature in the environment. Such compounds include known fragrances, insecticides, fumigants, disinfectants and mixtures thereof, wherein said mixtures are made up of compatible compounds which do not degrade or destroy the efficacy of each individual compound. Particularly preferred compounds are volatilizable fragrances such as those well-known in the art. Heat-stable volatile fragrances, which do not degrade when exposed to temperatures above 70° F., and which do not rapidly volatilize when exposed to an environment, possessing residual strength, are particularly efficacious.

A particularly preferred solid article for dispersing a volatilizable compound in an environment consists essentially of from about 25 to 30 wt. % initially particulate calcium sulfate having a loose bulk density of about 0.90 gm/cm$^3$;

about 25 to 30 wt. % initially particulate calcium sulfate having a loose bulk density of about 0.72 gm/cm$^3$;

about 2 to 4 wt. % initially particulate hydrous calcium sulfate having a loose bulk density of about 0.80 gm/cm$^3$;

about 0.5 to 1 wt. % emulsifier;

about 6 to 7 wt. % volatilizable compound; and about 30 to 35 wt. % water.

Use of this particularly preferred solid article in the method of dispersing a volatilizable compound in an environment comprises a particularly preferred method of effecting such dispersal. Exposure to said environment further comprising exposure to a gaseous flow, such as a convective or forced air flow, is also a more preferred practice of this method.

The optimum method and solid article for dispersing a volatilizable substance into an environment comprises exposing a solid article consisting essentially of about 28 wt. % initially particulate calcium sulfate having a loose bulk density of about 0.90 gm/cm$^3$;

about 28 wt. % initially particulate calcium sulfate having a loose bulk density of about 0.72 gm/cm$^3$;

about 2.9 wt. % initially particulate hydrous calcium sulfate having a loose bulk density of about 0.80 gm/cm$^3$;

about 0.6 wt. % emulsifier;

about 6.5 wt. % volatilizable compound; and about 33 wt. % water to said environment. Again, exposure to said environment wherein such exposure further comprises exposure to a gaseous flow, such as a convective or forced air flow, is also a more preferred practice of this method.

Use of a heat stable, volatilizable fragrance compound with either the particularly preferred or the optimum method, as part of the particularly preferred or optimum solid article composition, will effect a persistent, long-term dispersal and release of said fragrance into the environment. Such persistent release and dispersal as a result of this invention, continues for at least about 45 days, and may continue as long as about 90 days or longer, depending on the specific environment conditions. The approximate variation of persistence with the environment conditions is shown by the following table, which illustrates persistence of dispersion where the solid article is exposed to the environment (I), placed in a convective flow resulting from an incandescent lamp (II), and placed in a forced-air flow from a forced-air furnace (III) or air-conditioning unit:

| I | II | III |
|---|----|-----|
| CONDITIONS: | | |
| Ambient temp., relative humidity | Heat and convective air flow, elevated temp., lowered relative humidity | (a) Heat & forced air elevated temp., lowered relative humidity |
| | | (b) Cooling & forced air, lowered temp., lowered relative humidity |
| PERSISTENCE: | | |
| About 90 days | About 60 days or more | About 45 to 60 days or more |

The preferred process of making a solid article for dispersing a volatilizable compound in an environment comprises the steps of
(a) Combining from about 0.5 to 1 wt. % emulsifier and from about 6 to 7 wt. % of a volatilizable compound;
(b) Agitating and mixing said combined emulsifier and volatilizable compound until a uniform emulsion is formed;
(c) Combining with agitation the emulsion of step (b) with from about 30 to 35 wt. % water;
(d) Adding with agitation from about 2 to 4 wt. % particulate hydrous calcium sulfate having a loose bulk density of from about 0.75 to 0.85 gm/cm$^3$ to the mixture of step (c);
(e) Adding with agitation to the mixture of step (d) from about 25 to 30 wt. % particulate calcium sulfate having a loose bulk density of from about 0.85 to 0.95 gm/cm$^3$, and from about 25 to 30 wt. % particulate calcium sulfate having a loose bulk density of from about 0.70 to 0.75 gm/cm$^3$;
(f) Agitating the mixture of step (e) until a smooth slurry is formed;
(g) Placing said slurry in a molding zone; and
(h) Allowing said slurry to set in said molding zone until a solid article is formed.

Combination, mixing and agitation of the components may be carried out in any of the well-known mixing apparatus for industrial-scale manufacture. The mixing apparatus must be capable of adequately mixing and aerating the component slurry to assure formation of the microcellular structure on molding, yet must be controllable so as to avoid over-agitation and foaming. An antifoaming agent may be adding to the components during step (e) and (f) to prevent foaming and the incorporation of too much air into the slurry.

The molding zone into which the slurry is placed to form the solid article on setting may comprise any particle-type casting mold such as are well-known in the art. The solid article may be cast in any desired shape, with cylinders demonstrating particular efficacy for the purposes of the invention, which is believed to be due to the air flow characteristics of the cylinder's curvilinear surfaces. The slurry is poured into the mold and then allowed to stand until it sets, which is defined as the achieving of sufficient solidity that the solid article may be removed from the mold without deformation. A mold-releasing agent such as is known in the ceramic arts may be applied to the interior surfaces of the mold to ease release of the article on opening of the molds.

By utilization of this process with a heat-stable, volatilizable fragrance as the volatilizable compound, a solid article may be prepared which is a highly persistent, long-term source of pleasant fragrance for air deodorizing or odorizing in an environment, said effect lasting for 45 to 90 days. The level of odorizing or deodorizing activity can be heightened by placing said solid article in the convective flow path of an incandescent light bulb or in the forced flow path of a forced air heating or air-conditioning system.

A particularly preferred process for preparing a solid article of the invention comprises the steps of:
(a) Combining from about 0.5 to 1 wt. % emulsifier and from about 6 to 7 wt. % volatilizable compound;
(b) Agitating and mixing said combined emulsifier and volatilizable compound until a uniform emulsion is formed;
(c) Combining with agitation the emulsion of step (b) with from about 30 to 35 wt. % water;
(d) Adding with agitation from about 2 to 4 wt. % particulate hydrous calcium sulfate having a loose bulk density of about 0.80 gm/cm$^3$ to the mixture of step (c);
(e) Adding with agitation to the mixture of step (d) from about 25 to 30 wt. % particulate calcium sulfate having a loose bulk density of about 0.90 gm/cm$^3$, and from about 25 to 30 wt. % particulate calcium sulfate having a loose bulk density of about 0.72 gm/cm$^3$;
(f) Agitating the mixture of step (e) until a smooth slurry is formed;
(g) Placing said slurry in a molding zone; and
(h) Allowing said slurry to set in said molding zone until a solid article is formed.

The optimum process for preparing a solid article of the invention comprises the steps of:
(a) Combining about 0.6 wt. % emulsifier and about 6.5 wt. % volatilizable compound;
(b) Agitating and mixing said combined emulsifier and volatilizable compound until a uniform emulsion is formed;
(c) Combining with agitation the emulsion of step (b) with about 33 wt. % water;
(d) Adding with agitation about 2.9 wt. % particulate hydrous calcium sulfate having a loose bulk density of about 0.80 gm/cm$^3$ to the mixture of step (c);
(e) Adding with agitation to the mixture of step (d) about 28 wt. % particulate calcium sulfate having a loose bulk density of about 0.90 gm/cm$^3$, and about 28 wt. % particulate calcium sulfate having a loose bulk density of about 0.72 gm/cm$^3$;
(f) Agitating the mixture of step (e) until a smooth slurry is formed;
(g) Placing said slurry in a molding zone; and
(h) Allowing said slurry to set in said molding zone until a solid article is formed.

The products of these particularly preferred and optimum processes also demonstrate long-term persistence in dispersing the volatilizable compound to the environment.

Despite its improved long-term persistence without disintegration, crumbling or efflorescence, the solid article of the invention does, after the passage of time, cease to disperse the volatilizable compound. In commercial situations where it may be desired to store or inventory the solid articles of the invention, the period from preparation to use may long exceed the 45- to 90-day post-exposure period of efficacy of the article. Similarly, an individual who may wish to utilize such a product may wish to do so only at certain times of the year, yet may desire to maintain an article of the invention at hand for use on short notice. Again, this mandates avoidance of exposure to an environment from the time of preparation until the time of use.

To effect these aims, a kit for effecting dispersal of a volatilizable compound is provided, which comprises:
(1) a solid volatilizable compound-dispersing article consisting essentially of
from about 25 to 30 wt. % initially particulate calcium sulfate having a loose bulk density of from about 0.85 to 0.95 gm/cm$^3$;
about 25 to 30 wt. % initially particulate calcium sulfate having a loose bulk density of from about 0.70 to 0.75 gm/cm$^3$;
about 2 to 4 wt. % initially particulate hydrous calcium sulfate having a loose bulk density of from about 0.75 to 0.85 gm/cm$^3$;
about 0.5 to 1 wt. % emulsifier;
about 6 to 7 wt. % volatilizable compound; and
about 30 to 35 wt. % water; and
(2) package means slightly larger than said article, said means encasing said article, said means being sealed and being made of a flexible, tearable barrier film which seals upon the application of heat and pressure so that the envelope may be opened by being torn and being substantially impermeable to said volatilizable compound and the vapors thereof, and being of a strength to resist the vapor pressure thereof.

Figure 1:
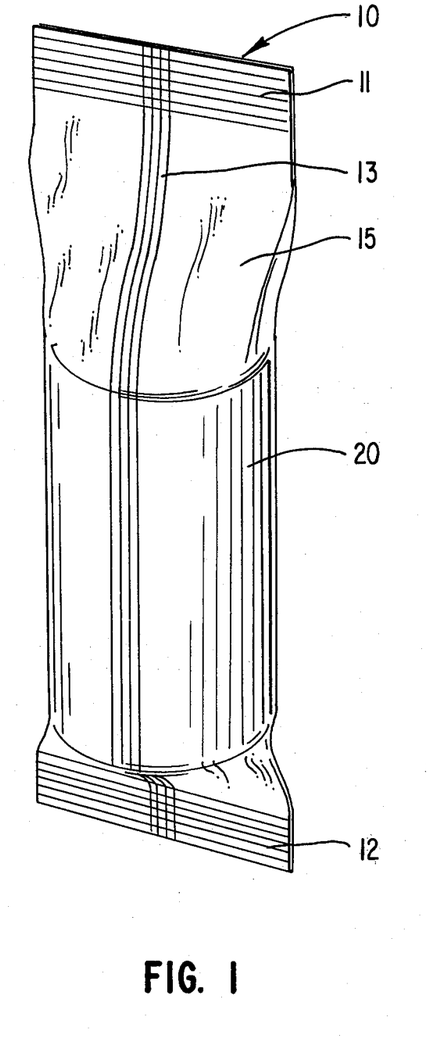
FIG. 1 is a perspective view of the sealed volatilizable compound dispersal kit.

The kit is illustrated in FIG. 1 of the drawing. The solid volatilizable compound-dispersing article 20 is wrapped in substantially impermeable package means 15, which package means are slightly larger than said article. This allows for the formation of an adequate but snugly fitting package, with minimal empty space resulting in the interior of the package when sealed around article 20 with seals 11, 12 and 13. Alternately, package means 15 may be in the form of an open-ended cylinder in which article 20 is inserted and which is thereafter sealed snugly around the article with seals 11, and 12 to form a closed package.

The snug fit of the packaging means allows only a very slight evaporation or vaporization of the volatilizable compound before an equilibrium of vapor pressure sets in, substantially halting any further loss of volatilizable compound from the article. The substantially impermeable package means also effectively hermetically seal the solid article from the environment, thus preventing exposure to the environment so as to maintain substantially undiminished the efficacy of the article during storage.

A wide variety of substantially gas and/or air impermeable packaging means are well-known in the art, particularly gas/moisture barrier films. Particularly efficacious are laminated barrier films and metal foil-polymer laminated film combinations, where the polymer film on the interior of the laminate affords heat and pressure sealing capabilities for the packaging. Useful barrier films include polypropylene/cellophane and polypropylene/cellophane/foil laminates manufactured by Olin Corporation, and Dow Chemical Company's polyethylene/saran Saranex films. Also useful are multi-layer packaging films such as Union Carbide Corporation's Perflux films, which may be utilized with or without lamination to a metal foil.

The packaging means chosen, particularly a barrier film or a polymer-lined metal foil, must be flexible, tearable and capable of sealing upon application of heat and pressure, so that the package may be opened by being torn. Any packaging means utilized must be compatible with the solid article such that the package is substantially unaffected by and substantially impermeable to the volatilizable compound and its vapors. The means must also be of sufficient strength to resist the vapor pressure of the compound under normally encountered atmospheric pressures and temperatures.

Particularly preferred and optimum kits of the invention comprise those wherein the solid volatilizable compound-dispersing article has the compositions set out at page 12, line 25–page 13, line 12 and page 13, line 20–page 14, line 6, respectively.

Figure 2:
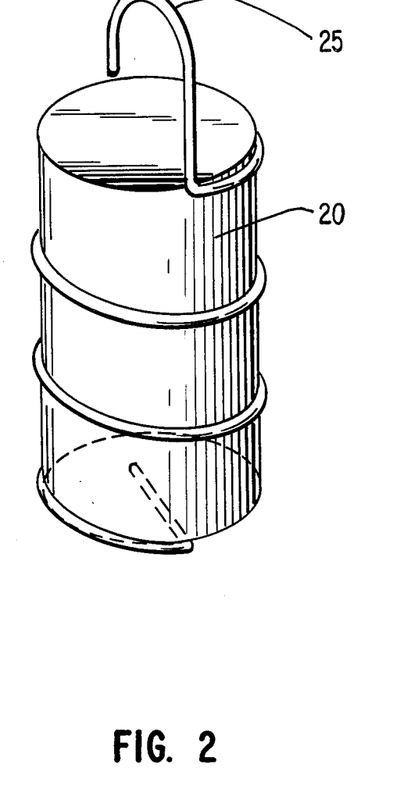
FIG. 2 is a perspective view of the solid article of the kit, after removal from the packaging means.

The kit may also be provided with solid article affixing means secured to the solid volatilizable compound dispersing article. These means are disposed to secure the solid article in any desired location in an environment. Hook means 25 are illustrated in FIG. 2, which are of particular use in fixing the article in a location in an environment where the solid article is exposed to a gaseous flow, such as within the convective flow of an incandescent bulb by hanging the article 20 by means 25 in a lamp, or within a forced flow of air, again by hanging the article 20 by means 25 in a heat or air-conditioning supply vent.

A kit in which the volatilizable compound is a heat-stable, volatilizable fragrance compound will demonstrate long shelf life with little or no loss of efficacy and, when the solid article is removed from the package means and exposed to the environment, will disperse a pleasant fragrance therethrough for a period of about 45 to about 90 days.

The following example illustrates the method and composition of the invention:

EXAMPLE

A solid article for dispersing a volatilizable compound in an environment was prepared as follows:
(a) About 0.6 wt. % of polyoxyethylene 20 sorbitan mono-oleate sold under the trade name "Tween 80" was combined with about 6.5 wt. % of a heat-stable, volatilizable fragrance reinforced with fixatives, solubilizers and extenders;
(b) The emulsifier and fragrance of step (a) was agitated and mixed until a uniform emulsion was formed, which occurred in about 10 to 20 seconds;
(c) The emulsion of step (b) was then combined with agitation with about 33 wt. % water;
(d) Continuing the agitation, about 2.9 wt. % of an essentially 100-mesh, particulate hydrous calcium sulfate, sold under the trade name "Terra Alba" and having a loose bulk density of about 0.80 gm/cm$^3$ was added to the emulsion of step (c), and the agitation was continued for at least 20 seconds;
(e) To the mixture of step (d) was then added about 28 wt. % of an essentially 100-mesh, particulate calcum sulfate sold by Georgia Pacific under the trade name "Industrial Plaster #51-0412," having a loose bulk density of about 0.72 gm/cm$^3$, and about 28 wt. % of a particulate calcium sulfate sold by U.S. Gypsum Co. under the trade name "Hydrocal White," having a loose bulk density of about 0.90 gm/cm$^3$;

(f) Rapid agitation of the mixture of step (e) was then effected at 1750 rpm agitator speed for at least 25 seconds, with an antifoaming compound being added to said mixture. Agitation was continued until a smooth slurry was formed;

(g) The slurry resulting from step (f) was then poured onto railroad molding equipment previously treated with a mold release agent, and the slurry was equally distributed into the mold openings;

(h) The slurry was allowed to stand in the molds until it set, a period of at least about 8 minutes. The resulting solid articles were then discharged from the mold by inverting and agitating same.

The resulting cylinders were then prepared in kit form by cutting said cylinders to desired lengths, and heat and pressure sealing said cylinder in a Saranex-14 (manufactured by Dow Chemical Company) barrier film strip. Several of the cylinder kits were maintained under average shelf-storage and warehouse conditions for 9 to 12 months; when the kits were opened and the cylinders exposed to the environment, they dispersed fragrance in a long-term persistent manner over at least a 45-day period.

Other cylinders were removed from the packaging means soon after preparation. Several cylinders were tested for fragrance dispersion characteristics by suspending over a lamp, having an incandescent bulb, by means of a spiral hook-bearing wire holder, while others were suspending in front of forced air heating vents. The data in Table I was determined, which generally illustrates the relationship of the fragrance dispersion action of the cylinders to heat, air flow and air relative humidity (R.H.) factors.

TABLE I

| Vent | | Lamp | |
|---|---|---|---|
| A. Furnace OFF | | A. Lamp OFF | |
| Vent Temperature | 70° F. | Inside Temperature | 70° F. |
| Vent R.H. | 40% | Inside R.H. | 40% |
| Fragrance Release | MINIMUM | Fragrance Release | MINIMUM |
| B. Furnace ON | | B. Lamp ON | |
| Vent Temperature | 120° F. | Inside Temperature | 95° F. |
| Vent R.H. | 10% | Inside R.H. | 20% |
| Fragrance Release | MAXIMUM | Fragrance Release | MEDIUM |

From this data, it may readily be seen that maximum dispersion occurs in hot, dry, flowing air, while minimum dispersion occurs in cool, humid air, essentially irrespective of air flow.

The cylinders tested as shown in Table I continued to disperse fragrance for at least 45 days.

Further tests were performed to note dispersion of cylinders on a forced-air vent during cooling. These results are set out in Table II, which illustrates that the low humidity air resulting from air conditioning, taken with the high cooling air flow rate, caused adequate dispersion of fragrance.

TABLE II

| Season | Heat./Air Vel. | | R.H. | Fragr. Rel./Inten. |
|---|---|---|---|---|
| Heating | Vent | 120° F. | 10% | MAXIMUM |
| Heating | Lamp | 95° F. | 15% | MEDIUM |
| Cooling | Vent | 60° F. | 45% | MEDIUM |
| Cooling | Lamp | 95° F. | 20% | MEDIUM |

The cylinders tested as shown in Table II also continued to disperse fragrance for at least 45 days.

While particular embodiments of the invention, and the best mode contemplated by the inventor for carrying out the invention, have been shown, it will be understood, of course, that the invention is not limited thereto since modifications may be made by those skilled in the art, particularly in light of the foregoing teachings. It is, therefore, contemplated by the appended claims to cover any such modifications as incorporate those features which constitute the essential features of these improvements within the true spirit and scope of the invention.

I claim:

1. A solid unitary article for dispersing a volatilizable compound consisting essentially of
   from about 25 to 30 wt. % initially particulate calcium sulfate having a loose bulk density of from about 0.85 to 0.95 gm/cm$^3$;
   about 25 to 30 wt. % initially particulate calcium sulfate having a loose bulk density of from about 0.70 to 0.75 gm/cm$^3$;
   about 2 to 4 wt. % initially particulate hydrous calcium sulfate having a loose bulk density of from about 0.75 to 0.85 gm/cm$^3$;
   about 0.5 to 1 wt. % emulsifier;
   about 6 to 7 wt. % volatilizable compound; and
   about 30 to 35 wt. % water.

2. The solid unitary article according to claim 1 consisting essentially of
   from about 25 to 30 wt. % initially particulate calcium sulfate having a loose bulk density of about 0.90 gm/cm$^3$;
   about 25 to 30 wt. % initially particulate calcium sulfate having a loose bulk density of about 0.72 gm/cm$^3$;
   about 2 to 4 wt. % initially particulate hydrous calcium sulfate having a loose bulk density of about 0.80 gm/cm$^3$;
   about 0.5 to 1 wt. % emulsifier;
   about 6 to 7 wt. % volatilizable compound; and
   about 30 to 35 wt. % water.

3. The solid unitary article according to claim 1 consisting essentially of:
   about 28 wt. % initially particulate calcium sulfate having a loose bulk density of about 0.90 gm/cm$^3$;
   about 28 wt. % initially particulate calcium sulfate having a loose bulk density of about 0.72 gm/cm$^3$;
   about 2.9 wt. % initially particulate hydrous calcium sulfate having a loose bulk density of about 0.80 gm/cm$^3$;
   about 0.6 wt. % emulsifier;
   about 6.5 wt. % volatilizable compound; and
   about 33 wt. % water.

4. The solid unitary article according to claim 1 wherein said volatilizable compound is a heat-stable, volatile fragrance compound.

5. The solid unitary article according to claim 2 wherein said volatilizable compound is a heat-stable, volatile fragrance compound.

6. The solid unitary article according to claim 3 wherein said volatilizable compound is a heat-stable, volatile fragrance compound.

7. A method of dispersing a volatilizable substance into an environment comprising exposing a solid unitary article consisting essentially of from about 25 to 30 wt. % initially particulate calcium sulfate having a loose bulk density of from about 0.85 to 0.95 gm/cm$^3$;

about 25 to 30 wt. % initially particulate calcium sulfate having a loose bulk density of from about 0.70 to 0.75 gm/cm$^3$;

about 2 to 4 wt. % initially particulate hydrous calcium sulfate having a loose bulk density of from about 0.75 to 0.85 gm/cm$^3$;

about 0.5 to 1 wt. % emulsifier;

about 6 to 7 wt. % volatilizable compound; and about 30 to 35 wt. % water to said environment.

8. The method of claim 7 wherein said solid unitary article consists essentially of from about 25 to 30 wt. % initially particulate calcium sulfate having a loose bulk density of about 0.90 gm/cm$^3$;

about 25 to 30 wt. % initially particulate calcium sulfate having a loose bulk density of about 0.72 gm/cm$^3$;

about 2 to 4 wt. % initially particulate hydrous calcium sulfate having a loose bulk density of about 0.80 gm/cm$^3$;

about 0.5 to 1 wt. % emulsifier;

about 6 to 7 wt. % volatilizable compound; and about 30 to 35 wt. % water.

9. The method of claim 7 wherein said solid unitary article consists essentially of about 28 wt. % initially particulate calcium sulfate having a loose bulk density of about 0.90 gm/cm$^3$;

about 28 wt. % initially particulate calcium sulfate having a loose bulk density of about 0.72 gm/cm$^3$;

about 2.9 wt. % initially particulate hydrous calcium sulfate having a loose bulk density of about 0.80 gm/cm$^3$;

about 0.6 wt. % emulsifier;

about 6.5 wt. % volatilizable compound; and about 33 wt. % water.

10. The method of claim 7 wherein said volatilizable compound is a heat-stable, volatile fragrance compound.

11. The method of claim 8 wherein said volatilizable compound is a heat-stable, volatile fragrance compound.

12. The method of claim 9 wherein said volatilizable compound is a heat-stable, volatile fragrance compound.

13. The method of claims 7, 8 or 9 wherein said solid unitary article is exposed to a gaseous flow in said environment.

14. The method of claims 7, 8 or 9 wherein said solid unitary article is exposed to a gaseous flow in said environment, said flow at least in part comprising convective flow resulting from the presence of a heat source in said environment.

15. The method of claims 7, 8 or 9 wherein said solid unitary article is exposed to a gaseous flow in said environment, said flow at least in part comprising forced flow from a gaseous source present in said environment.

16. The method of claims 10, 11 or 12 wherein said solid unitary article is exposed to a gaseous flow in said environment.

17. The method of claims 10, 11 or 12 wherein said solid unitary article is exposed to a gaseous flow in said environment, said flow at least in part comprising convective flow resulting from the presence of a heat source in said environment.

18. The methods of claims 10, 11 or 12 wherein said solid unitary article is exposed to a gaseous flow in said environment, said flow at least in part comprising forced flow from a gaseous source present in said environment.

19. The method of claims 7, 8, 9, 10, 11 or 12 wherein said solid unitary article is exposed to a gaseous flow in said environment, said flowing gas being air.

20. The method of claim 16 wherein said flowing gas is air.

21. The method of claim 17 wherein said flowing gas is air.

22. The method of claim 18 wherein said flowing gas is air.

23. The method of claim 19 wherein said flowing air is at a temperature higher than the ambient temperature of the environment.

24. A process of making a solid unitary article for dispersing a volatilizable compound comprising the steps of:

(a) Combining from about 0.5 to 1 wt. % emulsifier and from about 6 to 7 wt. % of a volatilizable compound;

(b) Agitating and mixing said combined emulsifier and volatilizable compound until a uniform emulsion is formed;

(c) Combining with agitation the emulsion of step (b) with from about 30 to 35 wt. % water;

(d) Adding with agitation from about 2 to 4 wt. % particulate hydrous calcium sulfate having a loose bulk density of from about 0.75 to 0.85 gm/cm$^3$ to the mixture of step (c);

(e) Adding with agitation to the mixture of step (d) from about 25 to 30 wt. % particulate calcium sulfate having a loose bulk density of from about 0.85 to 0.95 gm/cm$^3$, and from about 25 to 30 wt. % particulate calcium sulfate having a loose bulk density of from about 0.70 to 0.75 gm/cm$^3$;

(f) Agitating the mixture of step (e) until a smooth slurry is formed;

(g) Placing said slurry in a molding zone; and (h) Allowing said slurry to set in said molding zone until a solid unitary article is formed.

25. The process of claim 24 comprising the steps of:

(a) Combining from about 0.5 to 1 wt. % emulsifier and from about 6 to 7 wt. % volatilizable compound;

(b) Agitating and mixing said combined emulsifier and volatilizable compound until a uniform emulsion is formed;

(c) Combining with agitation the emulsion of step (b) with from about 30 to 35 wt. % water;

(d) Adding with agitation from about 2 to 4 wt. % particulate hydrous calcium sulfate having a loose bulk density of about 0.80 gm/cm$^3$ to the mixture of step (c);

(e) Adding with agitation to the mixture of step (d) from about 25 to 30 wt. % particulate calcium sulfate having a loose bulk density of about 0.90 gm/cm$^3$, and from about 25 to 30 wt. % particulate calcium sulfate having a loose bulk density of about 0.72 gm/cm$^3$;

(f) Agitating the mixture of step (e) until a smooth slurry is formed;

(g) Placing said slurry in a molding zone; and (h) Allowing said slurry to set in said molding zone until a solid unitary article is formed.

26. The process of claim 24 comprising the steps of:
(a) Combining about 0.6 wt. % emulsifier and about 6.5 wt. % volatilizable compound;
(b) Agitating and mixing said combined emulsifier and volatilizable compound until a uniform emulsion is formed;
(c) Combining with agitation the emulsion of step (b) with about 33 wt. % water;
(d) Adding with agitation about 2.9 wt. % particulate hydrous calcium sulfate having a loose bulk density of about 0.80 gm/cm$^3$ to the mixture of step (c);
(e) Adding with agitation to the mixture of step (d) about 28 wt. % particulate calcium sulfate having a loose bulk density of about 0.90 gm/cm$^3$, and about 28 wt. % particulate calcium sulfate having a loose bulk density of about 0.72 gm/cm$^3$;
(f) Agitating the mixture of step (e) until a smooth slurry is formed;
(g) Placing said slurry in a molding zone; and
(h) Allowing said slurry to set in said molding zone until a solid unitary article is formed.

27. The process of claims 24, 25 or 26 wherein said volatilizable compound is a heat-stable, volatile fragrance compound.

28. The process of claims 24, 25 or 26 wherein said molding zone is substantially cylindrical.

29. The process of claims 24, 25 or 26 wherein said volatilizable compound is selected from the group consisting of volatile fumigants, insecticides, disinfectants, fragrances and mixtures thereof.

30. A solid unitary article made by the process of claims 24, 25 or 26.

31. A kit for effecting dispersal of a volatilizable compound into an environment comprising:
(1) a solid unitary volatilizable compound dispersing article consisting essentially of
from about 25 to 30 wt. % initially particulate calcium sulfate having a loose bulk density of from about 0.85 to 0.95 gm/cm$^3$;
about 25 to 30 wt. % initially particulate calcium sulfate having a loose bulk density of from about 0.70 to 0.75 gm/cm$^3$;
about 2 to 4 wt. % initially particulate hydrous calcium sulfate having a loose bulk density of from about 0.75 to 0.85 gm/cm$^3$;
about 0.5 to 1 wt. % emulsifier;
about 6 to 7 wt. % volatilizable compound; and
about 30 to 35 wt. % water; and
(2) package means slightly larger than said article, said means encasing said article, said means being sealed and being made of a flexible, tearable barrier film which seals upon the application of heat and pressure so that the envelope may be opened by being torn and being substantially unaffected by and substantially impermeable to said volatilizable compound and the vapors thereof, and being of a strength to resist the vapor pressure thereof.

32. The kit according to claim 31 wherein said solid unitary volatilizable compound dispersing article consists essentially of
from about 25 to 30 wt. % initially particulate calcium sulfate having a loose bulk density of about 0.90 gm/cm$^3$;
about 25 to 30 wt. % initially particulate calcium sulfate having a loose bulk density of about 0.72 gm/cm$^3$;
about 2 to 4 wt. % initially particulate hydrous calcium sulfate having a loose bulk density of about 0.80 gm/cm$^3$;
about 0.5 to 1 wt. % emulsifier;
about 6 to 7 wt. % volatilizable compound; and
about 30 to 35 wt. % water.

33. The kit according to claim 31 wherein said solid unitary volatilizable compound dispersing article consists essentially of
about 28 wt. % initially particulate calcium sulfate having a loose bulk density of about 0.90 gm/cm$^3$;
about 28 wt. % initially particulate calcium sulfate having a loose bulk density of about 0.72 gm/cm$^3$;
about 2.9 wt. % initially particulate hydrous calcium sulfate having a loose bulk density of about 0.80 gm/cm$^3$;
about 0.6 wt. % emulsifier;
about 6.5 wt. % volatilizable compound; and
about 33 wt. % water.

34. The kit of claims 31, 32 or 33 wherein said volatilizable compound is a heat-stable, volatile fragrance compound.

35. The kit of claims 31, 32 or 33 wherein said kit further comprises solid unitary article affixing means, whereby said solid unitary article may be fixed in a location in an environment.

36. The kit of claim 35 wherein said affixing means are disposed such that said solid unitary article may be fixed in a location in an environment wherein said solid article is exposed to a gaseous flow.

37. The kit of claim 35 wherein said volatilizable compound is a heat stable, volatile fragrance compound.

38. The kit of claim 37 wherein said affixing means are disposed such that said solid unitary article may be fixed in a location in an environment wherein said solid unitary article is exposed to a gaseous flow.

* * * * *

UNITED STATES PATENT AND TRADEMARK OFFICE
CERTIFICATE OF CORRECTION

PATENT NO. : 4,285,905
DATED : August 25, 1981
INVENTOR(S) : Richard Feit

It is certified that error appears in the above—identified patent and that said Letters Patent are hereby corrected as shown below:

Column 1, line 44:

change "kwown" to read

-- known --

Column 4, line 38:

change "emulsifier" to read

-- emulsified --

Column 10, line 67:

change "calcum" to read

-- calcium --

UNITED STATES PATENT AND TRADEMARK OFFICE
CERTIFICATE OF CORRECTION

PATENT NO. : 4,285,905

DATED : August 25, 1981

INVENTOR(S) : Richard Feit

Page 2 of 2

It is certified that error appears in the above—identified patent and that said Letters Patent is hereby corrected as shown below:

Column 15, line 51:

change "saidarticle" to read

-- said article --

Signed and Sealed this

Eighteenth Day of May 1982

[SEAL]

Attest:

*Attesting Officer*

GERALD J. MOSSINGHOFF

*Commissioner of Patents and Trademarks*